United States Patent [19]

Pressman et al.

[11] Patent Number: 5,723,689
[45] Date of Patent: Mar. 3, 1998

[54] PROCESS FOR RECOVERING BISPHENOLS

[75] Inventors: Eric James Pressman, East Greenbush; Sheldon Jay Shafer, Clifton Park; Joseph Richard Wetzel, Latham, all of N.Y.; Martin Herke Oyevaar, Goes, Netherlands

[73] Assignee: General Electric Company, Schenectady, N.Y.

[21] Appl. No.: 587,052

[22] Filed: Jan. 16, 1996

[51] Int. Cl.[6] .......................... C07C 39/12; C07C 39/16; C07C 37/68
[52] U.S. Cl. .......................... 568/724; 568/722; 568/723
[58] Field of Search .......................... 568/722, 723, 568/724

[56] References Cited

U.S. PATENT DOCUMENTS 3,394,089  7/1968  McNutt et al. .
5,302,774  4/1994  Berg .
5,475,152  12/1995  Kissinger et al. .

OTHER PUBLICATIONS

"Bisphenol A", Encyclopedia of Chemical Processing and Design, 1977, pp. 406–430.

Kirk–Othmer, Encyclopedia of Chemical Technology, Fourth Edition, vol. 7, pp. 723–729, 1993.

*Primary Examiner*—Gary Geist
*Assistant Examiner*—Karl J. Puttlitz, Jr.
*Attorney, Agent, or Firm*—William H. Pittman

[57] ABSTRACT

A method for recovering substantially pure p,p-bisarylols from a mixture comprising the same by subjecting the mixture to vacuum distillation and melt crystallization in the absence of an adduct crystallization and the generation of a reaction recycle stream.

11 Claims, No Drawings

PROCESS FOR RECOVERING BISPHENOLS

FIELD OF THE INVENTION

This invention relates to a novel method for recovering substantially pure p,p-bisarylols. More particularly, the invention is directed to the recovery of p,p-bisphenols like 2,2-bis(4-hydroxyphenyl)propane (BpA) by subjecting a mixture comprising the same to a method that does not require, among other things, adduct crystallizations and the generation of reaction recycle streams.

1. Background of the Invention

Polycarbonates are a well known class of high impact resistant thermoplastic resins characterized by optical clarity, high ductility as well as other advantageous properties. They are frequently employed as lenses and windows as a result of their transparency. Bisphenol A polycarbonate is the predominant commercially available resin of this type. It ordinarily has a glass transition temperature of about 150° C. and is derived from 2,2-bis(4-hydroxyphenyl)propane.

The 2,2-bis(4-hydroxyphenyl)propane, for example, are commercially available and typically prepared from phenols and acetone by methods which employ promoters and catalysts comprising hydrochloric acid or catalysts comprising sulfonated ion exchange resins. Such methods characteristically require cumbersome, costly and potentially hazardous processing steps in order to recover the desired bisphenol.

It is of increasing interest to recover p,p-bisarylols by methods that do not require adverse processing steps. The instant invention, therefore, is directed to a novel method for recovering substantially pure p,p-bisarylols that does not require, among other things, adduct crystallizations and the generation of reaction recycle streams.

2. Description of the Prior Art

Efforts have been disclosed for preparing BPA monomers. In U.S. Pat. No. 3,394,089, BPA monomers are prepared from a ketone and phenol in the presence of a strong-acid cation-exchange resin.

Other efforts for preparing BPA monomers have been disclosed. In the *Encyclopedia of Chemical processing and Design* Vol. 4, pages 407–430 (1977), the preparation of BPA is described.

SUMMARY OF THE INVENTION

The instant invention is directed to a method for recovering substantially pure p,p-bisarylols comprising the steps of:

(a) vacuum distilling a mixture comprising p,p-bisarylols to produce a distillate and residue; and (b) subjecting the residue to melt crystallization to obtain the substantially pure p,p-bisarylol.

In the instant invention, it has been unexpectedly discovered that substantially pure p,p-bisarylols may be recovered from mixtures comprising the same in the absence of adduct crystallizations and without the generation of reaction recycle streams. Substantially pure is defined herein as at least about 90% pure and preferably at least about 95% pure and most preferably at least about 99% pure. Reaction recycle stream is defined herein to mean a stream comprising impurities fed back to further react in the process which is the source of the mixture comprising the p,p-bisarylols.

DETAILED DESCRIPTION OF THE PREFERRED EMBODIMENTS

There is essentially no limitation with respect to the type of p,p-bisarylols recovered in this invention. Often, they are represented by the formula $$HO-A^1-Y_t-A^2-OH$$

wherein $A^1$ and $A^2$ are each independently a divalent substituted or unsubstituted aromatic radical and Y is a bridging radical such as a hydrocarbon radical and particularly a saturated radical such as methylene, cyclohexylmethylene, 2-[2.2.1]-bicycloheptylmethylene, ethylene, isopropylidene, neopentylidene, cyclohexlidene, cyclopentadecylidene, cyclododecylidene or adamantylidene, especially a gem-alkylene (alkylidene) radical and most often $C(R)_2$ wherein each R is independently a $C_{1-5}$ alkyl and preferably a methyl group. The value for t is 0 or 1.

Illustrative non-limiting examples of the p,p-bisarylols represented by the formula above include:

2,2-bis(4-hydroxyphenyl)propane (bisphenol A);
2,2-bis(3,5-dibromo-4-hydroxyphenyl)propane;
2,2-bis(3,5-dimethyl-4-hydroxyphenyl)propane;
1,1-bis(4-hydroxyphenyl)cyclohexane;
1,1-bis(3,5-dimethyl-4-hydroxyphenyl)cyclohexane;
1,1-bis(4-hydroxyphenyl)decane;
1,4-bis(4-hydroxyphenyl)propane;
1,1-bis(4-hydroxyphenyl)cyclododecane;
1,1-bis(3,5-dimethyl-4-hydroxyphenyl)cyclododecane;
4,4-dihydroxydiphenyl ether;
4,4-thiodiphenol;
4,4-dihydroxy-3,3-dichlorodiphenyl ether; and
4,4-dihydroxy-3,3-dihydroxydiphenyl ether
9,9-bis-(4-hydroxyphenyl)fluorene There is essentially no limitation with respect to the origin of the mixtures comprising the p,p-bisarylols which are recovered in this invention. The only proviso regarding the mixtures is that they are preferably generated from processes that are generally employed to make the p,p-bisarylols which are to be recovered in substantially pure form via this invention.

For example, the mixtures employed in this invention may be the reaction mixtures generated from processes which react arylols like phenol and ketones like acetone to form BPA. Such processes are often conducted by feeding the acetone and phenol along with a bulk (added at once with reactants) promoter like 3-mercaptopropionic acid to reactors which contain acidic ion exchange resin catalysts like sulfonated polystyrene. Often, when preparing the p,p-bisarylols to be recovered in this invention, no more than about 35 moles and preferably no more than about 25 moles and most preferably no more than about 15 moles of arylol are employed for every mole of ketone.

A more detailed description for the preparation of BPA utilizing 3-mercaptopropionic acid may be found in U.S. Pat. No. 2,468,982, the disclosure of which is incorporated herein by reference.

Additionally, it is within the scope of the instant invention to employ mixtures comprising p,p-bisarylols that have been prepared via methods which add any of the conventional bulk promoters effective in acid catalyzed condensations. Such bulk promoters include methyl or ethyl mercaptans and they too may be added along with the arylols and ketones fed to the reactors comprising the acidic ion exchange resin catalysts.

In a preferred embodiment of this invention, it is desirable to utilize a mixture which has been generated from a process that first treats the acidic ion exchange resin catalysts with a sulfur-comprising promoter prior to the addition of any arylols or ketones to the reactor. In such a case, the sulfur comprising promoter is an attached promoter which is defined herein to mean that the promoter is either covalently or ionically linked/bonded to the acid ion exchange resin catalyst.

There is essentially no limitation with respect what sulfur-comprising promoters are attached to the acidic ion exchange resin catalysts other than that subsequent to attachment, a mercaptan is available to promote the reaction. Often, the promoter is attached to the resin via, for instance, an ammonium sulfonate linkage or a sulfonamide linkage. Illustrative examples of the sulfur-comprising promoters which may be employed include $C_{1-4}$ aminoalkanethiols; especially 2-aminoethanethiol.

The treatment of the acid ion exchange resin catalysts may be carried out by adding promoter to an aqueous slurry of the resin catalyst and thereby attaching the promoter to the catalyst. A more detailed description of the treatment of the catalyst may be found in U.S. Pat. No. 3,394,089, the disclosure of which is incorporated herein by reference.

Subsequent to attaching the sulfur comprising promoter to the acidic ion exchange resin catalysts, the catalyst is often referred to as being partially neutralized. When partially neutralized, often no more than about 50% and preferably no more than about 20% of all acid groups on the acidic ion exchange resin catalysts are neutralized.

In the most preferred embodiment of this invention, the mixtures comprising the p,p-bisarylols to be recovered in substantially pure form are prepared from methods which utilize the catalysts with attached promoters as described above as well as staged ketone additions.

Such staged ketone additions are defined herein to mean that when the arylols and ketones are fed to the reactor(s) comprising the catalyst with attached promoters, no more than about 50% and preferably no more than about 30% and most preferably no more than about 10% of the total moles of ketone employed are fed to the reactor at the start of the condensation reaction, and up to about 65% of all moles of ketone employed are fed to the reactor(s) after the condensation reaction reaches no more than about 70% completion. Any remaining ketone is added thereafter.

There is no particular limitation with respect to what form the mixtures comprising the p,p-bisarylols are in prior to performing the steps described in (a) and (b). Said mixtures comprising the p,p-bisarylols may therefore be solids, melts or solutions.

Typically, the mixtures in this invention subject to the steps described in (a) and (b) further comprise o,p-BPA, chromans like 4-(3,4-dihydro-2,4,4-trimethyl-2H-1-benzopyran-2-yl)-phenol and 4-(3,4-dihydro-2,2,4-trimethyl-2H-1-benzopyran-2-yl)-phenol and trisarylols like 2,4-bis[1-(4-hydroxyphenyl)-1-methylethyl]-phenol. However, they preferably consist essentially of p,p-BPA, o,p-BPA, chromans like 4-(3,4-dihydro-2,4,4-trimethyl-2H-1-benzopyran-2-yl)-phenol and 4-(3,4-dihydro-2,2,4-trimethyl-2H-1-benzopyran-2-yl)-phenol and trisarylols like 2,4-bis[1-(4-hydroxyphenyl)-1-methylethyl]phenol.

When conducting the instant invention, the mixtures comprising the p,p-bisarylols are first fed to a set-up/apparatus which is capable of enabling the mixture comprising the p,p-bisarylols to be distilled to produce a residue enriched in p,p-bisarylols. Such a setup/apparatus is not limited and it is often one which comprises a vacuum source, heat source, distillation flask and a condenser.

There is essentially no limitation with respect to the temperature at which the distillation takes place other than that the temperature is not one which causes disintergration of the p,p-bisarylols and is not greater than the boiling point of the p,p-bisarylols at the pressure the distillation takes place. The pressure at which the distillation takes place is often no more than about 300 torr and preferably no more than about 100 torr and most preferably no more than about 10 torr.

Subsequent to the distillation step, the resulting residue comprising p,p-bisarylols is melt crystallized. Any apparatus capable of removing impurities from a melt of the residue may be employed. Often, the melt crystallization is achieved via a zone melting or zone refining apparatus. Such an apparatus often comprises a means for freezing and melting the residue. The melting and freezing temperatures at which the residue is subjected to are those which allow for substantially pure p,p-bisarylols to crystallize and impurities to collect in the resulting molten phase. An illustrative example of such an apparatus may be found in *Modern Methods of Chemical Analysis* (1968), pages 15–16, the disclosure of which is incorporated herein by reference.

The following example is provided to further illustrate and facilitate the understanding of the instant invention. All products obtained may be confirmed via conventional techniques including proton and carbon-13 magnetic resonance spectroscopy, infrared spectroscopy and x-ray techniques.

EXAMPLE

An attached promoter sulfonated polystyrene resin catalyst was prepared by mechanically stirring for about 4 hours and under a nitrogen over pressure 7.5 parts of (1.75% aqueous) aminoethanethiol hydrochloride and 1 part sulfonated polystyrene resin (Amberlite®131). The resulting attached promoter catalyst (approximately 20% of the sulfonic acid groups on the resin neutralized) was washed copiously with water and vacuum dried overnight at a temperature of about 80° C., pressure about 20 torr.

A reaction vessel equipped with a pump, reactant reservoir, heated reactant column with capacity for staged ketone additions and glass column having approximately 10g of the attached promoter catalyst was charged with a 36:1 mole ratio feed of phenol to acetone. The feed moved in the direction from reactant reservoir to heated reactant column to glass column. The glass column ( with upward flow capability) was maintained at about 70° C. As the reaction proceeded, acetone was added in two staged additions separated by the removal (distillation) of $H_2O$ until the $H_2O$ content of the residue was about 1000–1500 ppm. After the additional acetone additions, the final phenol to acetone mole ratio was 12:1.

A similar resulting mixture comprising p,p-BPA (about 95%), o,p-BPA (about 3.5%) and chromans (about 0.30%) was distilled via vacuum distillation [pressure 4.5 torr (bottom), 2.7 torr (top), temperature 230° C. (bottom), 210° C. (top)] to remove phenol, o,p-BPA and chromans. The resulting residue (p,p-BPA enriched) was fed to a zone refining apparatus for melt crystallization The resulting final product, p,p-BPA was greater than 99.9% pure, indicating that a substantially pure product could be obtained in the absence of adduct crystallizations and without the generation of reaction recycle streams.

What is claimed is:

1. A method for recovering bisphenol A in the absence of adduct crystallizations and without the generation of reaction recycle streams, said method comprising the steps of:
   (a) vacuum distilling a mixture comprising A to produce a distillate comprising o,p-bisphenol A, chromans and triarylols and a residue; and (b) subjecting the residue to melt crystallization to obtain bisphenol A which is at least about 99% pure.

2. A method in accordance with claim 1 wherein said mixture comprising bisphenol A is generated in a condensation reaction between phenol and acetone in the presence of a promoter and an acidic ion exchange resin catalyst.

3. A method in accordance with claim 2 wherein said acidic ion resin catalyst is sulfonated polystyrene.

4. A method in accordance with claim 2 wherein said promoter is a bulk additive which is 3-mercaptopropionic acid.

5. A method in accordance with claim 2 wherein said promoter is an attached promoter and bonded to said sulfonated polystyrene to neutralize acidic groups present thereon.

6. A method in accordance with claim 5 wherein no more than about 50% of all acidic groups on the sulfonated polystyrene are neutralized.

7. A method in accordance with claim 5 wherein said attached promoter is a $C_{1-4}$ aminoalkanethiol.

8. A method in accordance with claim 7 wherein said $C_{1-4}$ aminoalkanethiol is 2-aminoethanethiol.

9. A method in accordance with claim 1 wherein the vacuum distilling occurs at a pressure of no more than about 300 torr.

10. A method in accordance with claim 1 wherein said vacuum distilling occurs at a pressure of no more than about 10 torr.

11. A method in accordance with claim 1 wherein said melt crystallization is accomplished via a zone melting or zone refining apparatus.

* * * * *